(12) United States Patent
Jacobsen et al.

(10) Patent No.: US 6,579,246 B2
(45) Date of Patent: Jun. 17, 2003

(54) CORONARY GUIDEWIRE SYSTEM

(75) Inventors: Stephen C. Jacobsen, Salt Lake City, UT (US); Clark C. Davis, Salt Lake City, UT (US); David L. Wells, Salt Lake City, UT (US)

(73) Assignee: Sarcos, LC, Salt Lake City, UT (US)

( * ) Notice: Subject to any disclaimer, the term of this patent is extended or adjusted under 35 U.S.C. 154(b) by 0 days.

(21) Appl. No.: 09/746,738

(22) Filed: Dec. 22, 2000

(65) Prior Publication Data

US 2002/0013540 A1 Jan. 31, 2002

Related U.S. Application Data

(60) Provisional application No. 60/171,838, filed on Dec. 22, 1999.

(51) Int. Cl.[7] .................................................. A61B 5/00
(52) U.S. Cl. ........................................................ 600/585
(58) Field of Search ................................. 600/434, 435, 600/585

(56) References Cited

U.S. PATENT DOCUMENTS

| | | | |
|---|---|---|---|
| 3,625,200 A | 12/1971 | Muller | |
| 4,020,829 A | 5/1977 | Willson et al. | |
| 4,215,703 A | 8/1980 | Willson | |
| 4,545,390 A | 10/1985 | Leary | |
| 4,811,743 A | 3/1989 | Stevens | |
| 4,832,047 A | 5/1989 | Sepetka et al. | |
| 4,884,579 A | 12/1989 | Engleson | |
| 4,911,148 A | 3/1990 | Sosnowski et al. | |
| 4,955,862 A | 9/1990 | Sepetka | |
| 4,964,409 A | 10/1990 | Tremulis | |
| 4,989,608 A | 2/1991 | Ratner | |
| 4,994,069 A | 2/1991 | Ritchart et al. | |
| 4,998,923 A | 3/1991 | Samson et al. | |
| 5,052,404 A | 10/1991 | Hodgson | |
| 5,095,915 A | * 3/1992 | Engleson | 600/585 |
| 5,106,455 A | 4/1992 | Jacobsen et al. | |
| 5,125,395 A | 6/1992 | Adair | |
| 5,147,317 A | 9/1992 | Shank et al. | |
| 5,254,106 A | 10/1993 | Feaster | |
| 5,256,144 A | 10/1993 | Kraus et al. | |
| 5,267,979 A | 12/1993 | Appling et al. | |
| 5,304,131 A | 4/1994 | Paskar | |
| 5,306,252 A | 4/1994 | Yutori et al. | |
| 5,315,996 A | 5/1994 | Lundquist | |
| 5,334,145 A | 8/1994 | Lundquist et al. | |
| 5,345,945 A | 9/1994 | Hodgson et al. | |
| 5,365,942 A | 11/1994 | Shank | |
| 5,376,084 A | 12/1994 | Bacich et al. | |
| 5,406,960 A | 4/1995 | Corso, Jr. | |
| 5,437,288 A | * 8/1995 | Schwartz et al. | 128/772 |
| 5,438,993 A | 8/1995 | Lynch et al. | |
| 5,439,000 A | 8/1995 | Gunderson et al. | |

(List continued on next page.)

FOREIGN PATENT DOCUMENTS

| | | |
|---|---|---|
| DE | 2539191 A1 | 3/1976 |
| EP | 0521595 B1 | 2/1992 |
| EP | 0790066 A2 | 2/1992 |
| EP | 0 608 853 A2 | 1/1994 |
| EP | 0937481 A1 | 2/1999 |
| WO | PCT/US91/07878 | 10/1991 |
| WO | PCT/US92/07619 | 9/1992 |
| WO | PCT/IB95/00075 | 2/1995 |
| WO | PCT/US98/16100 | 8/1998 |

*Primary Examiner*—Max F. Hindenburg
(74) *Attorney, Agent, or Firm*—Thorpe North & Western

(57) ABSTRACT

A guidewire system configured for introduction into a body lumen, comprising a core wire having proximal end and a distal end and a tapering profile, and a micromachined tube coupled to the core wire, and a joint where the micromachined tube is joined to the core wire; the location of the joint being at a location on the tapering profile where the torsional force which can be transferred by the core wire and the micromachined tubing are substantially the same.

54 Claims, 11 Drawing Sheets

U.S. PATENT DOCUMENTS

| | | |
|---|---|---|
| 5,441,483 A | 8/1995 | Avitall |
| 5,441,489 A | 8/1995 | Utsumi et al. |
| 5,477,856 A | 12/1995 | Lundquist |
| 5,507,751 A | 4/1996 | Goode et al. |
| 5,520,194 A | 5/1996 | Miyata et al. |
| 5,569,197 A | 10/1996 | Helmus et al. |
| 5,569,218 A | 10/1996 | Berg |
| 5,573,520 A | 11/1996 | Schwartz et al. |
| 5,666,969 A | 9/1997 | Urick et al. |
| 5,682,894 A | 11/1997 | Orr et al. |
| 5,746,701 A | 5/1998 | Noone |
| 5,833,632 A * | 11/1998 | Jacobsen et al. ............ 600/585 |
| 5,897,537 A | 4/1999 | Berg et al. |
| 5,935,108 A | 8/1999 | Katoh et al. |
| 6,004,279 A * | 12/1999 | Crowley et al. ............ 600/585 |

* cited by examiner

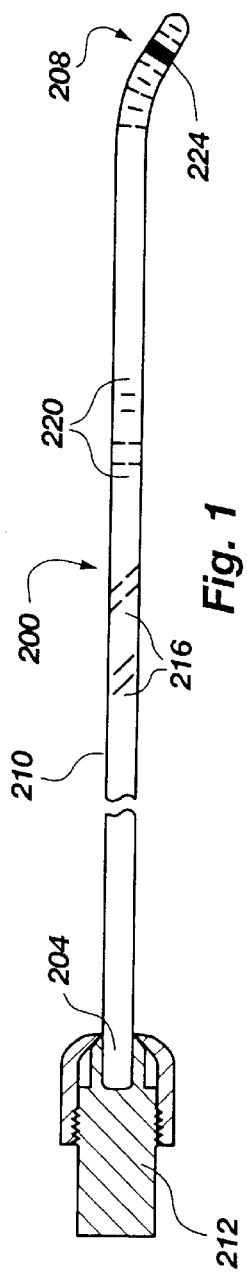
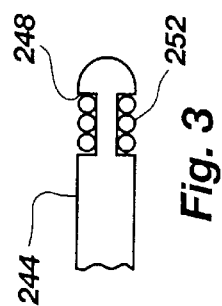
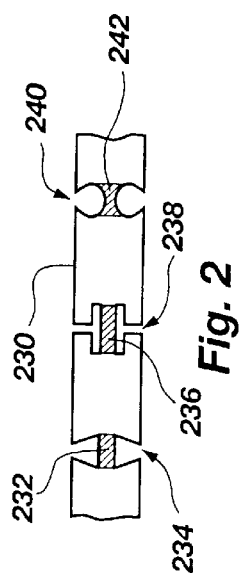
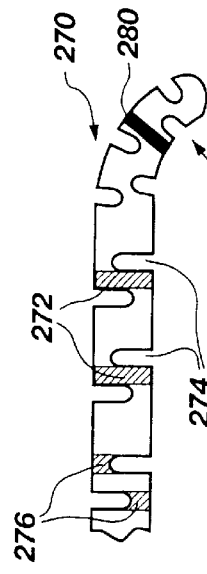
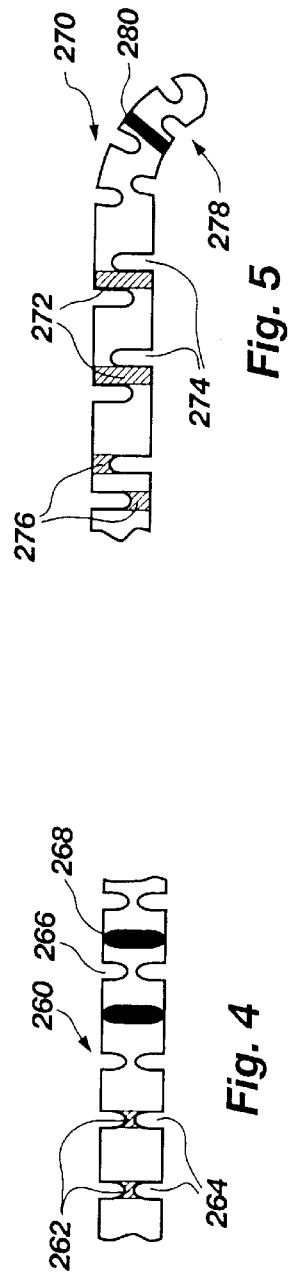
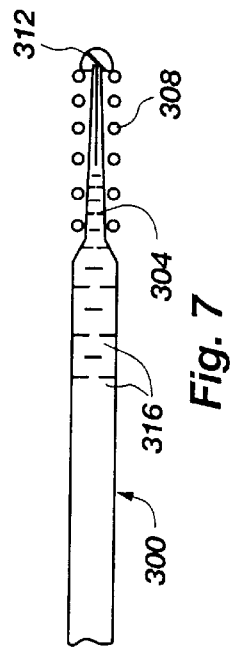
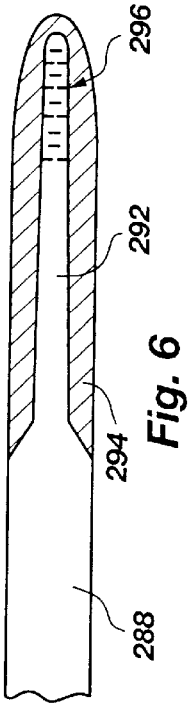

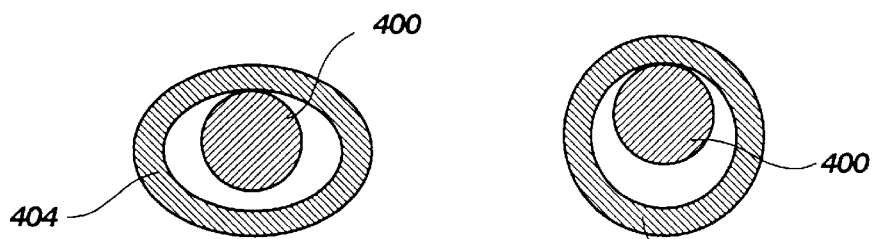
*Fig. 12a*
*Fig. 12b*
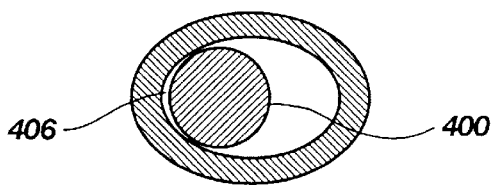
*Fig. 12c*
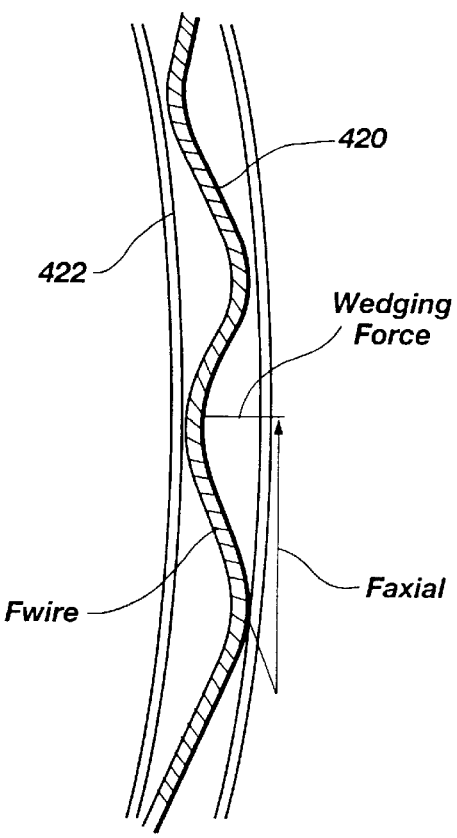
*Fig. 12d*

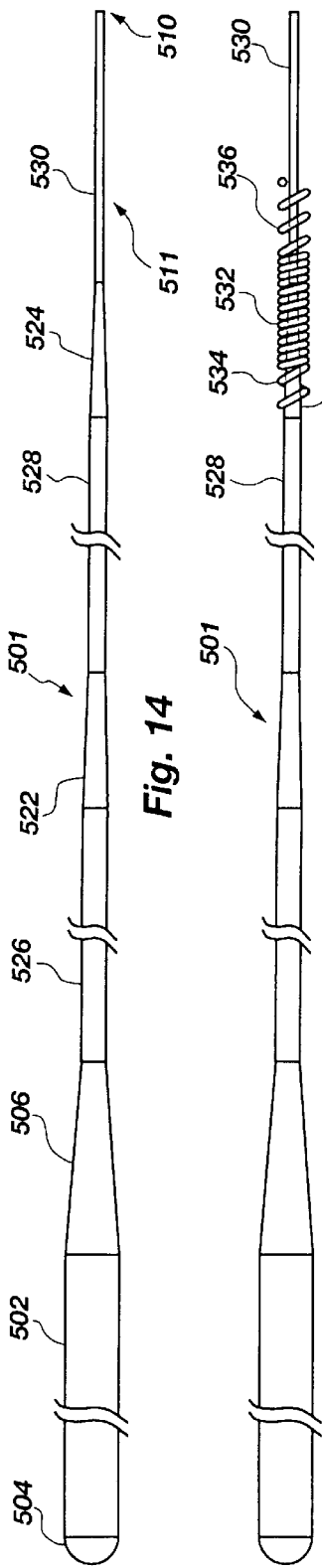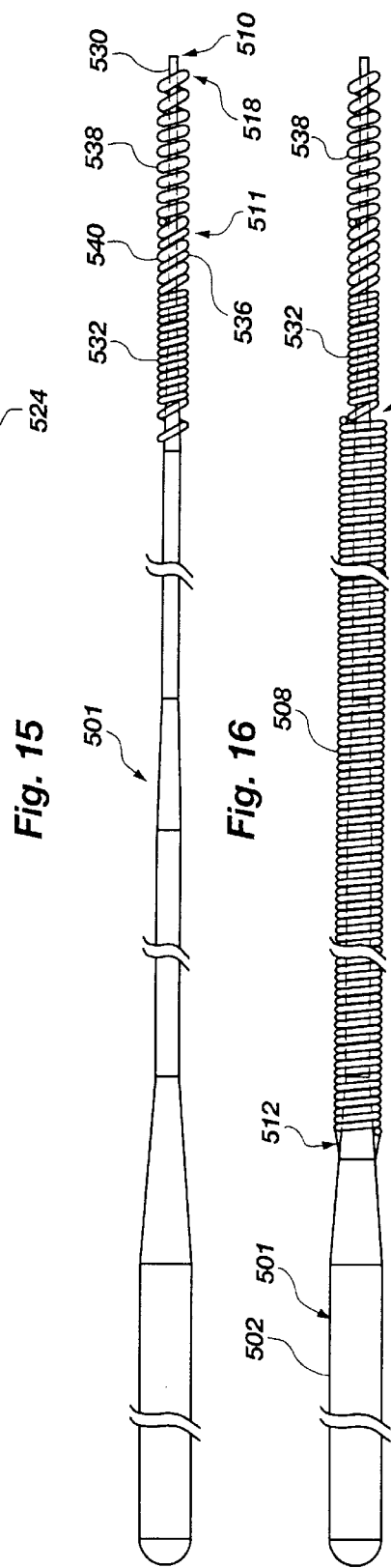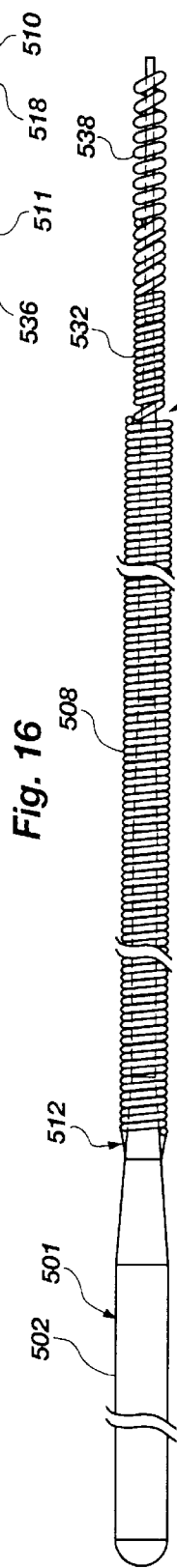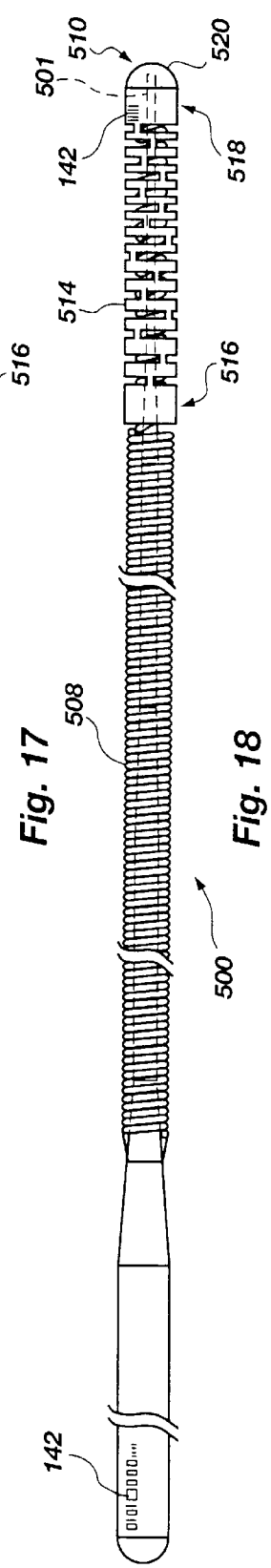

CORONARY GUIDEWIRE SYSTEM

This application claims priority of U.S. Provisional Application No. 60/171,383, filed Dec. 22, 1999.

BACKGROUND OF THE INVENTION

1. Field of the Invention

This invention relates to catheters and catheter guidewire apparatus and methods for making same. More specifically, the present invention relates to a guidewire apparatus with improved torque and flexure characteristics.

2. State of the Art

Catheter guidewires have been used for many years to "lead" or "guide" catheters to target locations in animal and human anatomy. This is typically done via a body lumen, for example such as traversing Luminal spaces defined by the vasculature to the target location. The typical conventional guidewire is from about 135 centimeters to 195 centimeters in length, and is made from two primary components—a stainless steel core wire, and a platinum alloy coil spring. The core wire is tapered on the distal end to increase its flexibility. The coil spring is typically soldered to the core wire at a point where the inside diameter of the coil spring matches the outside diameter of the core wire. Platinum is selected for the coil spring because it provides radiopacity for better fluoroscopic or other radiologic imaging during navigation of the guidewire in the body, and it is biocompatible. The coil spring also provides softness for the tip of the guidewire to reduce the likelihood of unwanted puncture of a luminal wall or the damaging of this and/or other anatomy.

As mentioned, navigation of a guidewire through the anatomy is usually achieved with the assistance of radiographic imaging. This is conventionally done by introducing contrast media into the body lumen being traversed and viewing the guidewire in the body lumen using X-ray fluoroscopy or other comparable methods. A guiding catheter can be used, as well as a catheter configured to perform a procedure and to be directed to the target location by the guidewire. Catheters to perform coronary angioplasty and/or deploy stents are examples.

The guidewire is provided with a tip that is curved or otherwise bent to a desired angle so as to deviate laterally a relatively short distance. By rotation of the wire, the tip can be made to deviate in a selected direction from an axis of the guidewire about which it rotates. The catheter is advanced over the guidewire or the guidewire is inserted into a catheter so that the guidewire and the catheter cooperate to reach the target location. The guidewire can be advanced so that its distal end protrudes out the distal end of the catheter, and also pulled back in a proximal direction so as to be retracted into the catheter. The catheter enables introduction of contrast media at the location of the distal tip to enable the visualization of a Luminal space being traversed by the catheter and guidewire. The guidewire or catheter/guidewire combination are introduced into a luminal space such as a blood vessel and advanced therethrough until the guidewire tip reaches a desired luminal branch. The user then twists the proximal end of the guidewire so as to rotate and point the curved distal tip into the desired branch so that the device may be advanced further into the anatomy via the luminal branch. The catheter is advanced over the guidewire to follow, or track, the wire. This procedure is repeated as needed to guide the wire and overlying catheter to the desired target location. The catheter accordingly provides a means to introduce contrast media, and also provides additional support for the wire. Once the catheter has been advanced to the desired location, the guidewire may be withdrawn, depending upon the therapy to be performed. Oftentimes, such as in the case of balloon angioplasty, the guidewire is left in place during the procedure and can be used to exchange catheters.

As is known, a guidewire having a relatively low resistance to flexure yet relatively high torsional strength is most desirable. As the guidewire is advanced into the anatomy, internal frictional resistance resulting from the typically numerous turns and attendant surface contacts, decreases the ability to turn the guidewire and to advance the guidewire further within the luminal space. This, in turn, may lead to a more difficult and prolonged procedure, or, more seriously, failure to access the desired anatomy at the target location and thus a failed procedure. A guidewire with high flexibility helps overcome the problems created by this internal resistance. However, if the guidewire does not also have good torque characteristics (torsional stiffness), the user will not be able to twist the proximal end in order to rotate the distal tip of the guidewire to guide its advance as required.

Among the approaches suggested in the prior art for increasing the flexibility of the tip of a guidewire is that of cutting axially spaced grooves in and near the tip, with the depths of the grooves increasing toward the tip. See, for example, U.S. Pat. No. 5,437,288. Increasing the flexibility of a tubular member for use in catheter applications by making cuts therein is also known. The use of cuts to increase flexibility on one side only of a tubular guidewire is disclosed, for example, in U.S. Pat. No. 5,411,483. However, these prior art approaches do not inform the art how to increase the flexibility of the guidewire without also significantly diminishing its torsional stiffness. The result can be a guidewire with a machined portion that is very flexible, but which also has very low torsional strength.

SUMMARY OF THE INVENTION

It has been recognized that it would be desirable to have a guidewire that is very flexible at its distal tip, yet which retains a relatively high degree of torsional stiffness, facilitating its use and manipulation.

A catheter guidewire apparatus in accordance with principles of the invention comprises a thin elongate body of material having an longitudinal axis, and which is formed so as to define at a proximal portion a wire, and at a distal portion a configuration comprising a plurality of integrally formed beams disposed along the length of the thin elongate body. The integral beams extend axially and transversely of the body and are positioned and formed to give the guidewire flexibility while maintaining a relatively high degree of torsional stiffness. By manipulating the size, shape, spacing, and orientation of the beams, the torsional stiffness of the guidewire relative to its flexibility or beam stiffness can be selectively altered. These beams comprise the portions of the wall of a tubular body, or the outer portions adjacent the outer surface of a solid body member, which remain after cuts are machined into the body.

In more detail, in order to optimize the performance of the guidewire transverse and axial beams adjacent one to another are configured so that the strain (deformation) in the adjacent axial and transverse beams as defined above is as nearly as possible equal in magnitude when the guidewire is subjected to torsional and bending forces resulting from twisting and bending of the apparatus. The resistance to fatigue failure of the axial and transverse beams can also be matched, since a procedure can involve numerous repetitions of deformation of the beam elements as the guidewire is turned and advanced in tortuous anatomy, and the deformations can be large, this is also a good methodology to optimize performance. Combining the methods, and/or using the one that yields the best performance for a particular application results in improved performance over prior guidewires.

In a further more detailed aspect, the beams can be formed between cuts, by making cuts in pairs substantially opposite from one another and substantially parallel to each other. The spacing and depth of the cuts comprising the cut pairs being adapted to provide desired maximum flexibility while sacrificing minimal torsional strength.

In further detail, the elongate member with beams formed therein can be polished and corners rounded to minimize stress concentrations and increase resistance to fatigue.

Other features and advantages of the invention will be apparent from the following detailed description, taken in conjunction with the accompanying drawings, which illustrate, by way of example, the features of the invention.

BRIEF DESCRIPTION OF THE DRAWINGS

FIG. 1 is a side, fragmented, partially crossectional, view of one embodiment of a catheter guidewire apparatus configured in accordance with the principles of the present invention;

FIG. 2 is a side, fragmented, view of a portion of a guidewire showing different types of cuts or etchings which may be utilized in a solid or tubular guidewire in accordance with principles of the present invention;

FIG. 3 is a side, fragmented, view of the tip of a guidewire with radiopaque coil or band wrapped thereabout, in accordance with principles of the present invention;

FIGS. 4 and 5 show side, fragmented views of two embodiments of guidewires formed with cuts, in accordance with principles of the present invention;

FIG. 6 is a side, fragmented view of a tapered guidewire formed with cuts, in accordance with principles of the present invention;

FIG. 7 is a side, fragmented view of a solid guidewire formed with a coiled tip, in accordance with principles of the present invention;

FIGS. 12a, 12b, and 12c show cross-sectional views of guidewires disposed within lumens of circular and elliptical catheters;

FIG. 12d shows the potential serpentine path of a guidewire through a catheter which tends to wedge the guidewire within the catheter;

FIG. 14 shows a side view, partially fragmented, of a core wire of the guidewire of FIG. 13 illustrating the grind profile;

FIG. 15 shows a side view, partially fragmented, of a core wire of the guidewire of FIG. 13 with a medial stainless steel wire coil added;

FIG. 16 shows a side view, partially fragmented, of a core wire of the guidewire of FIG. 13 with a medial wire coil and distal marker coil added;

FIG. 17 shows a side view, partially fragmented, of a core wire of the guidewire of FIG. 13 with a medial wire coil and distal marker coil and proximal stainless coil added;

FIG. 18 shows a side view, partially fragmented, of a core wire of the guidewire of FIG. 13 with a medial wire coil, distal marker coil, proximal stainless coil and micromachined tubing added at a distal tip portion;

DETAILED DESCRIPTION OF THE PREFERRED EMBODIMENT(S)

Figure 8:
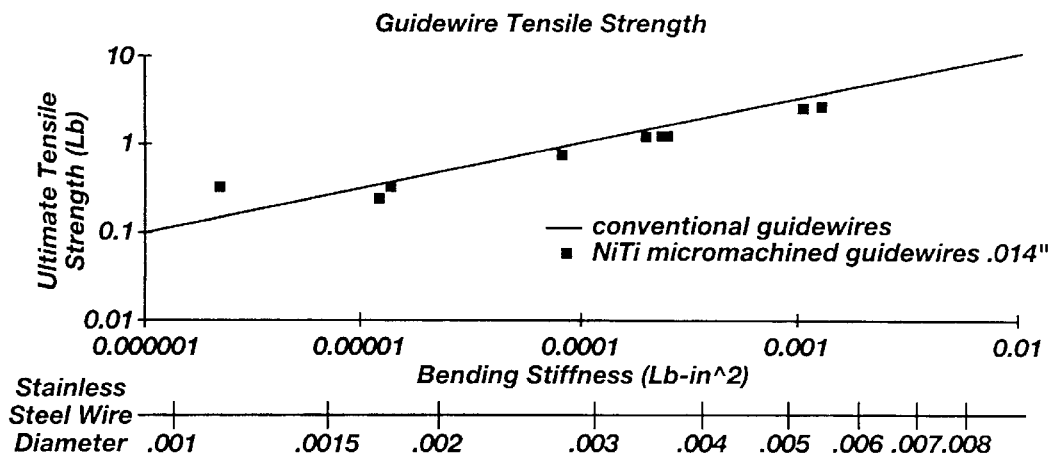
FIG. 8 is a graph of guidewire tensile strength compared to bending stiffness for a micromachined guidewire in accordance with principles of the present invention.

With reference to FIG. 1 of the drawings which illustrates one embodiment of a solid guidewire 200 made in accordance with the present invention. The guidewire 200 includes a proximal end 204 a distal end 208, and a midportion 210 disposed therebetween, with the proximal end being mounted in a conventional pin vise type torquing chuck 212. The guidewire 200 is preferably constructed of a material including nickel titanium alloy, and may range in size from about 0.008 inches to about 0.090 inches in diameter and from about 135 to 300 centimeters in length. The guidewire 200 can also be made of other materials, for example stainless steel. Four conventional preferred diameter sizes are 0.008 inches, 0.014 inches, 0.016 inches and 0.035 inches.

Cuts, slots, gaps or openings 216 and 220 are formed in the guidewire 200 along the length thereof, including the midportion 210, either by saw cutting (e.g., by a diamond grit embedded semiconductor dicing blade), etching (for example using the etching process described in U.S. Pat. No. 5,106,455), laser cutting, or electron discharge machining. The cuts 216 are angled to allow for a longer cut and thus greater flexibility, whereas cuts 220 are generally perpendicular to the longitudinal axis (long dimension) of the guidewire.

As will be discussed in more detail below, the cuts are specifically configured to form transverse and axial beams therebetween within the body of the guidewire. This configuration allows the cuts and beams to interact to provide for lateral flexibility in the guidewire, while maintaining improved torsional stiffness. By controlling and varying the spacing, depth and type of cuts, the flexure profile and torsional stiffness of the guidewire may be selectively and relatively independently modified. Generally, the more closely spaced the cuts and the greater their depth, the more flexible will be the guidewire. However, modification of the exact shape, orientation, and spacing of the cuts will also allow selective modification of flexibility while preserving the desired torsional characteristics of the member.

The distal end 208 of the guidewire 200 may be preshaped with a curve, as shown, to allow for directing the guidewire around curves and bends. To maintain flexibility in the distal end 208, cuts may also be provided on that end. Advantageously, the tip is rounded to minimize the chance of trauma to body tissue. Also formed on the distal end 208 is a radiopaque marker or band 224. The band 224 may be gold or platinum alloy (for X-ray fluoroscopy) or gadolinium or dysprosium, or compounds thereof (for MRI) and may be formed on the distal end 208 by deposition, wrapping or use of shape memory alloy (NiTi) effect to "lock" the band in place around the end.

With reference to FIG. 2 illustrating a portion of another exemplary guidewire 230, three different examples of types of cuts 234, 238 and 240 can be appreciated. These types of cuts provide a kind of built-in flexure "stop" to prevent further flexure of the guidewire when sides of these cut openings close to contact one another and prevent further flexure in that direction. Wedge shaped cuts 234 may be formed on opposite sides of the guidewire 230, with the greater width of the wedge being at the bottom of the cut. T-shaped cuts 238 may likewise be formed on opposite sides of the guidewire 230, with the cross piece of the T being at the bottom of the cut. Cuts 240 are generally circular as shown. It will be apparent that other cut shapes could also be provided to meet the needs of the user. The cuts 234, 238, and 240 are shown oppositely oriented, but it will be apparent that the cuts could also be formed at circumferentially-spaced locations about the guidewire, or at alternating locations such as shown and described in more detail with regard to, for example, FIG. 5.

All three types of cuts shown in FIG. 2 form an integral axial beam section, shown in cross-hatch as areas 232, 236, and 242, respectively, between oppositely disposed cuts. This configuration provides at least two distinct benefits. First, it allows the beam section to be longer than the gap of the flexure stop. This allows the amount of strain in the beam prior to stop engagement to be controlled by varying the ratio of beam length to gap size, allowing more flexibility, i.e. less bending resistance.

However, the location and shape of the beam section 232, 236, or 242 also greatly influences the torsional characteristics of the guidewire 230. As is well known by those skilled in mechanics, torsional strength is primarily provided by the outer portion of the cross section of a member. Thus, for illustration, a relatively thin-walled pipe will have nearly the same torsional strength as a solid bar of the same diameter because the central portion of the cross section of the solid bar contributes relatively little to torsional strength. Similarly, in providing an axial beam which crosses the entire cross-section of the guidewire 230, the portion of the beam sections 232, 236, or 242 comprising the outer portion of the cross section of the guidewire are most important in efficiently transmitting torque. Also, the axial beams are more or less effective in transmitting torsional forces from one side to the other of the cuts 234, 238, and 240 depending on their shape.

For example, beam 232 is relatively long (measured in the direction of the long axis of the guidewire), but is relatively deep (measured transverse to the long axis) and will therefore transmit a relatively large amount of torsional force. Beam 236 is longer and thinner than beam 232, and will therefore transmit a smaller amount of torsional force across the cut 238. Of the examples given in FIG. 2, beam 242 is the shortest and configured to transmit the greatest amount of torsional force. However, given the size and shape of cuts 240, this configuration may provide the greatest flexibility. Because the small flexure stop gaps of cuts 234, 238, and 240 may be varied in width without changing the depth or overall shape of the cut, the flexibility of the guidewire section may be selectively altered without affecting the size or strength of the axial beam section. Thus, the flexibility and torsional strength of the guidewire may be selectively and relatively independently altered.

Advantageously, longitudinally adjacent pairs of cuts may be rotated with respect to each other by about 80–90 degrees around the axis of the wire provide flexure laterally in multiple directions. However, the cuts may be located to provide preferential flexure in only one, two, three, etc. directions, if that is desired. Of course, the cuts could be randomly formed to allow bending (flex) equally, non-preferentially in all directions or planes. This could be achieved by circumferentially spacing the cuts.

FIG. 3 illustrates an alternative embodiment for applying a radiopaque marker to the distal end of a guidewire 244, shown in side, fragmented view. An annular trough or channel 248 is formed at the tip of the guidewire 244, and a radiopaque wire coil, preferably made of platinum alloy, is wound about the guidewire in the channel. The coil 252 could be welded or soldered to itself and/or the guidewire to hold it in place at the tip of the guidewire 244. If, in an alternate example, a gold or platinum band rather than a coil is used with a nickel titanium alloy guidewire, the guidewire could be cooled and deformed to allow the band to be placed on the wire and then when the guidewire is returned to room temperature, the band would be maintained in place on the guidewire without the need for welding or soldering or other joining mechanism. The same is true for a coil, except for joining the coil to itself.

FIG. 4 is a side, fragmented view illustrating a solid guidewire 260 formed with opposing cuts 262, 264 spaced along a portion of the guidewire, and opposed cuts 266, 268 rotated 90 degrees from said opposed cuts 262, 264. As with cuts 262, 264 the rotated cuts 266, 268 are preferably arranged in opposing pairs, with opposite cut 266 corresponding to 268 not visible on the far side of the guidewire. Of course, the cuts could be formed to provide preferential bending (flex) in one plane, or could be positioned to allow bending in multiple planes. This could be achieved, for example, by rotating adjacent pairs of cuts by 45 degrees with respect to one another or some other selected angular amount 0–90 degrees. Also shaded in FIG. 4 are the transverse beam sections 263 between adjacent opposing cuts 262, 264. It will be apparent that the pairs of rotated cuts 266, 268 will also form transverse beams therebetween, except that these beams will be oriented at an angle of 90 degrees relative to the beams 263.

FIG. 5 is a side, fragmented view of a solid guidewire 270 formed with staggered or offset cuts 274, 275 on opposite sides of the guidewire. A curved distal end 278 is also includes a radiopaque marker band 280. As with the FIG. 4 embodiment, certain pairs of offset cuts could be rotated with respect to the other pairs, to thereby control direction of flexure. This configuration also presents particular advantages regarding torsional control. As is evident from FIG. 4, opposed cuts produce thin flexure transverse beams 272 between each pair of opposed cuts. The dimensions and flexure properties of these beams are determined by the depth and separation of the cuts and so the flexibility of a guidewire with opposed cuts may be controlled by varying these parameters as well as the width of the cuts.

Offset cuts, as indicated in FIG. 5, produce much larger flexure beams 272 in the area between each pair of adjacent cuts. As will be expected, these large beams are able to transmit a relatively large amount of torsion. Depending on the depth of the cuts 274, this section will also comprise relatively thin axial beams 276 between the base of each cut and the opposing side of the guidewire.

It will be apparent that the flexure properties of this guidewire are determined not only by the depth and width of the cuts (as with opposed cuts) but also by the offset (axial spacing) of the cuts. Consequently, the flexibility of a guidewire with offset cuts can be controlled by varying any or all of these parameters. Also, the flexibility could be varied simply by controlling the degree of the offset while keeping the depth and width of the cuts constant.

FIG. 6 is a side, fragmented view of a solid guidewire 284 having an enlarged proximal section 288, which provides more torquability, and a narrowed distal section 292, covered by a hydrophilic polymer sleeve 294. For example, the enlarged section could be 0.014 inches in diameter whereas the narrowed section could be 0.010 inches in diameter. The distal end 296 of the guidewire 284 is formed with cuts as earlier described. Of course, cuts could also be provided at other locations in the narrowed section 292 or in the enlarged section 288, to increase flexibility, while maintaining high torsional stiffness.

FIG. 7 is a side, fragmented view of a solid guidewire 300 having a tapered distal end 304 about which is wrapped a coil 308 made, for example, of platinum alloy. Disposed at the tip of the distal end 304 of the guidewire and in the end of the coil 308 is a solder ball 312. Cuts 316 may also be formed in the guidewire 300 as discussed earlier. In addition to the use of cuts to control the flexure of a guidewire, nickel titanium alloy guidewires can be heat treated to vary the flexure characteristics. For example, selective annealing along the length of the wire can change stress/strain relationship of the material, and thus the flexure.

In the embodiments of a solid guidewire discussed above, the guidewires can be made "flow directable" by providing highly flexible distal ends. "Flow directability" means that the distal end of the guidewire tends to "flow" with the blood around curves and bends in a vasculature passageway. To reduce resistance to movement of a guidewire in a vasculature passageway, the surface of the guidewire may be electropolished to increase the smoothness thereof, and additionally, a lubricious coating may be applied to the surface of the guidewire—such coatings might illustratively include silicone based oil and/or polymer or hydrophilic polymers. Alternatively, a lubricious sleeve made, for example, of a hydrophilic polymer could also be provided for disposal over the guidewire. Such polishing has the additional benefit of increasing fatigue failure resistance.

FIGS. 8–11 provide graphical representation of the improvement this invention provides over conventional prior art devices. These graphs depict comparative test results of catheter guidewires formed according to this invention, showing the strength of catheter guidewires in accordance with principles of the invention compared to prior art devices, and the relative preservation of torsional strength relative to flexibility.

FIG. 8 is a graph of guidewire tensile strength compared to bending stiffness for the micromachined guidewire of the present invention. The individual (square) data points represent tension test results for micromachined guidewires. The ultimate tensile strength in pounds is indicated on the vertical axis, while the bending stiffness in psi is given on the horizontal axis. Below the horizontal axis is a second axis noting the size of stainless steel wire which would correspond to the respective bending stiffness shown in the horizontal axis. The solid line represents the theoretical tensile strength for equivalent solid wires.

This figure shows that micromachining cuts in the surface of the guidewire does not significantly reduce its tensile strength compared to non-machined guidewires for the same lateral bending stiffness. This is an important consideration in the catheter field because lower tensile strength could increase the likelihood of breakage of the guidewire during a procedure, or while attempting to extract the guidewire from a patient compared with conventional wires.

Figure 9:
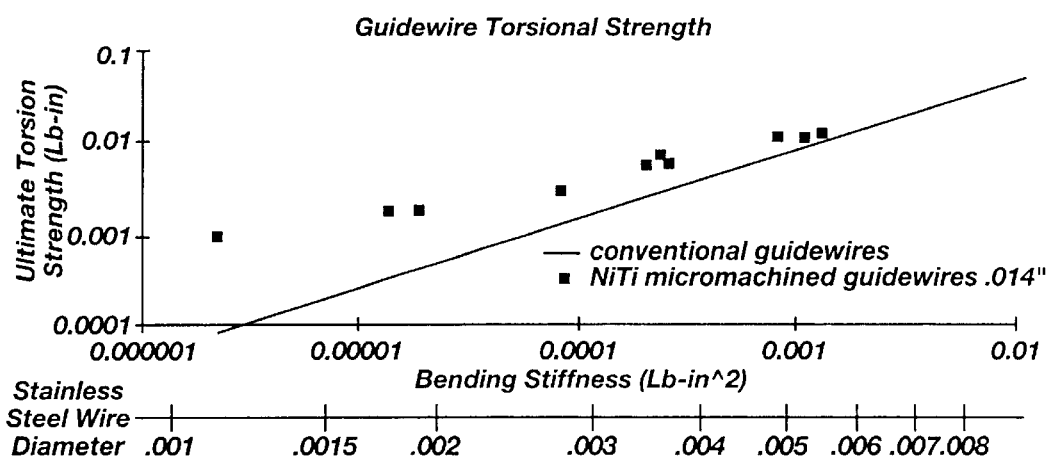
FIG. 9 is a graph of the ultimate torsional strength of a micromachined guidewire in accordance with principles of the present invention compared to its bending stiffness.
Figure 10:
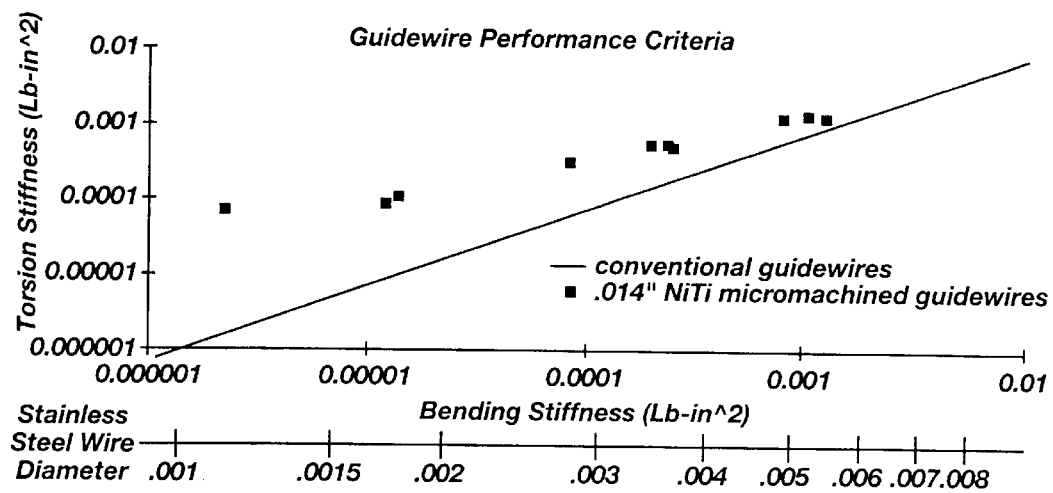
FIG. 10 is a graph of the torsional stiffiess of a micromachined guidewire in accordance with principles of the present invention compared to its bending stiffness.

FIG. 9 is a graph showing ultimate torsional strength of the micromachined guidewire of the present invention compared to its bending stiffness. The vertical axis shows the ultimate torsional strength of the guidewire in units of pound-inches, and the horizontal axis shows the bending stiffness in psi. As with FIG. 8, the square data points represent actual test results of micromachined catheter guidewires, and the solid line represents the theoretical results for a catheter guidewire of solid circular cross section. It will be apparent from this graph that as the bending stiffness (or size) of the conventional guidewire decreases, the expected or theoretical torsional strength also decreases. This is depicted by the solid line. However, as the actual test results indicate, as the size or bending strength of the micromachined guidewire decreases, the torsional strength does not correspondingly decrease as would be expected. Instead, as can be seen from the divergence of the data points from the solid line, the torsional strength of the guidewire decreases at a much slower rate. This situation is depicted in a slightly different way in FIG. 10, which provides a graph of the bending stiffness of the micromachined guidewire of the present invention compared to its torsional stiffness in psi. Again, the actual results diverge from the expected results for smaller and more flexible guidewires.

Figure 11:
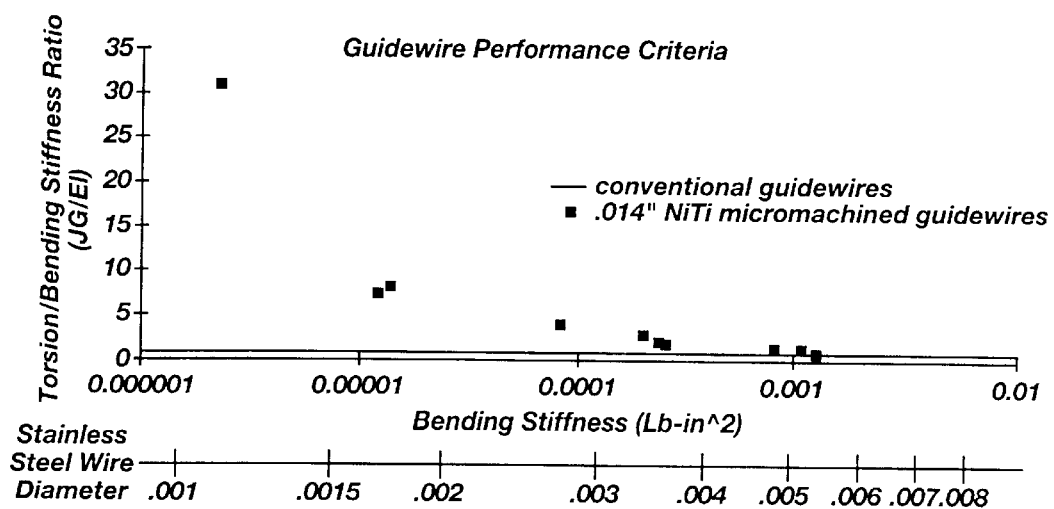
FIG. 11 is a graph showing the ratio of torsional stiffness to bending stiffness of a micromachined guidewire in accordance with principles of the present invention compared to its bending stiffness.

The importance of this situation is most clearly evident from FIG. 11, which is a graph showing the ratio of torsional stiffness to bending stiffness of the micromachined guidewire of the present invention compared to its bending stiffness. In this graph the vertical axis represents a ratio of torsional stiffness to bending stiffness (JG/EI), with the result that the expected relationship of bending stiffness to torsional stiffness (the solid line) is now a horizontal line. In FIG. 11, this line is set equal to unity, in order to more graphically show the actual results of the inventors' tests. As can be seen from these actual test results, as the flexure strength decreased, the torsional strength of the micromachined guidewires was more than 30 times more than expected.

The condition indicated by FIG. 11 represents some unexpected results. When the inventors first began micromachining catheter guidewires, as with the prior art, the goal was primarily to increase the flexibility. However, as guidewire sizes decreased and/or flexibility increased, the inventors noticed a corresponding (and expected) decrease in torsional strength. This is a significant problem with catheter guidewires because guidewires with low torsional strength cannot be manipulated as easily, and are more likely to become wedged or jammed into the catheter or vasculature of the patient. With a torsionally weak guidewire, when the user twists the proximal end, there is a significant delay in the transmission of the torque to the distal end. Indeed, like axially twisting the end of a weak coil spring, most of the torque is not transmitted at all. Instead, the geometry of the guidewire is likely to be deformed into a serpentine shape and wedge into the side of the catheter or vasculature in which it is located.

FIG. 12 shows cross-sectional views of guidewires disposed within the lumen of circular and elliptical catheters. As will be apparent, when a circular catheter is advanced into the vasculature of a patient and navigates curves and other tortuous routes, the cross-sectional shape of the catheter frequently tends to flatten out in places into a more elliptical cross-section. When a guidewire 400 is disposed in catheter 402 having a circular cross-section, it would have no preference as to its location within the cross section—its position will present a state of physical equilibrium regardless of its location because all locations are the same. However, with an elliptical catheter 404, the guidewire 400 in a central location represents a state of unstable equilibrium, like a ball sitting on the top of another ball. The result is that the guidewire will naturally gravitate to a point of stable equilibrium 406, in the tight corner of the catheter lumen. In this condition, it can be seen that the area of contact between the guidewire and the catheter is much larger, resulting in large frictional forces which will hinder the easy movement of the guidewire within the catheter.

Figure 13:
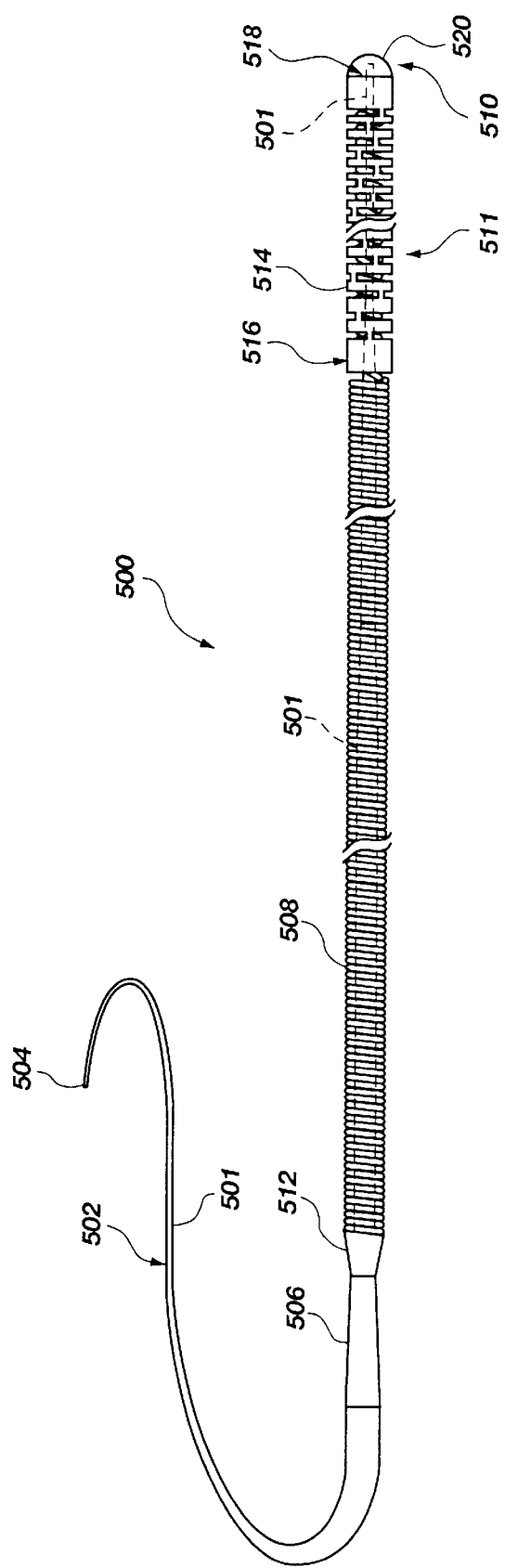
FIG. 13 shows a perspective, partially fragmented, view of a guidewire in accordance with principles of the invention in another embodiment.

This condition will also tend to wedge the guidewire within the catheter simply by virtue of the serpentine shape. FIG. 13 shows the potential serpentine path of a torqued guidewire 420 through a catheter 422. By virtue of the deformation of the guidewire 420, when an axial driving force (denoted Fwire in FIG. 13) is applied to the guidewire 420, it will be converted into an axial force (denoted Faxial) and a perpendicularly oriented wedging force (denoted Wedging Force) which will tend to jam the guidewire within the catheter.

To prevent these problems, the inventors experimented with methods of providing cuts in catheter guidewires that would increase flexibility without reducing torsional strength as much. It was hoped that for a guidewire of a given flexibility, the torsional strength could be increased by 50% above the theoretical or predicted torsional strength. After trying many configurations, the inventors discovered that forming cuts in the guidewires so as to create beams with a particular location and configuration would allow flexibility to be increased without a correspondingly large decrease in torsional strength. The inventors were pleasantly surprised when testing the present invention to find that instead of a 50% increase of torsional strength, they had found a way to provide a more than 3000% increase in torsional strength. As a result, guidewires formed by the present method provide significantly greater torsional strength relative to their flexibility than the prior art.

With reference to FIG. 13 an exemplary guidewire 500 in accordance with principles of the invention, and giving the advantages discussed above, comprises a proximal portion 502 extending from a proximal end 504 to a first transition portion 506 where the diameter of the guidewire changes. This proximal portion comprises a stainless steel core wire 501 configured as solid wire of circular cross section. The core wire in the proximal portion is covered with a low friction coating. For example PTFE is used to coat the proximal portion in the illustrated example. The proximal portion has a diameter as large as needed to transmit torque sufficient for the intended use of the guidewire. For coronary and some peripheral uses, for example, a diameter of about 14 thousandths of an inch is appropriate, and is used in the illustrated example.

At the first transition portion 506 the stainless steel wire is ground to a smaller diameter, transitioning over an axial length sufficient to provide a smooth transition. This is about 2 inches in one embodiment. Beginning at a distal end of the first transition portion the guidewire 500 has a more complex configuration. A proximal coil 508 is disposed over the stainless core wire 501. The core wire continues to the distal end 510 of the guidewire, the proximal coil overlaying the core wire as will be further explained. The proximal coil is attached to the core wire at the first transition portion 506 by a proximal solder joint 512 at a point where the inner diameter of the coil matches the outer diameter of the core wire. The diameter of the core wire continues to decrease under the proximal coil, and beyond it in accordance with a grind profile that will be described below.

At a distal end of the proximal coil 508 the guidewire 500 in an exterior aspect comprises a micromachined tubing 514 formed of a material comprising a superelastic material such as NiTi alloy. This micromachined tubing is very important to functionality of the catheter guidewire, as it transmits torque to the distal end 510 of the guidewire but is very flexible. The micromachined tubing overlays additional structure as will be described below. The micromachined tubing is attached to the proximal coil 508 via other underlying structure, and the core wire 501 at a medial solder and glue joint 516. The location of this joint is important as it is the point where the torsional force "carrying capacity" of the core wire 501 is substantially equal to that of the micromachined tubing. A force path is therefore established which extends through the core wire from the proximal end 504 of the guidewire 500 to the medial solder and glue joint 516, then continues through the micromachined tubing 514 to the distal end 510 of the guidewire 500.

As can be appreciated, the view of FIG. 13 is fragmented, and not to scale. The outer diameter of the proximal coil 508 is substantially the same as the proximal portion 502 of the core wire. The outer diameter of the micromachined tubing 514 at the distal tip portion 511 of the guidewire 500 is also approximately the same, all being about 14 thousandths of an inch. In one embodiment the proximal coil is about 11 inches long and the distal tip portion comprising the micromachined tubing is about 2 inches long. The distal tip portion can be given a curved or other bent configuration is known in the art.

At the distal end 150 of the guidewire 500 the micromachined tubing, underlying structure (not shown), and the core wire 501 are attached at a distal solder and glue joint 518. The core wire has a very small diameter at the distal end, the grind profile reducing it to approximately 2 thousandths of an inch prior to reaching that point. The distal solder and glue joint comprises an adhesive 520 which is formed into a rounded configuration at the distal end of the guidewire to form an a-traumatic tip.

Turning to FIGS. 14–18 the construction of an exemplary guidewire configuration will be described in more detail. With reference particularly to FIG. 14, the core wire 501 alone is seen to advantage, with the grind profile appreciable. The corewire has a rounded configuration at the proximal end 504 of the wire, and the proximal portion 502 is as previously described, and is about 65 inches in length in one exemplary embodiment. The grind profile extends about 14 inches further to the distal end 510 of the guidewire 500. In addition to the first transition portion 506, a second 522, and a third 524, transition portion are provided. Distal of the first transition, which as mentioned is about 2 inches in length in the exemplary illustrated embodiment, the core wire has a first reduced diameter portion 526 having a length of about 6 inches and a diameter of about seven and a half thousandths of an inch. The second transition portion is also about 2 inches in length, and the diameter further reduces from that of the first reduced diameter portion to about five and a half thousandths of an inch. This diameter is maintained for about two and a half inches, to form a second reduced diameter portion 528. At the third transition portion 524 the diameter further decreases to about two thousands of an inch, which is maintained to the distal end 510 as mentioned, to form a third reduced diameter portion 530. This third transition portion is about one tenth of an inch in length, and the third reduced diameter portion is about one and nine tenths inches in length in the illustrated exemplary embodiment. The third reduced diameter portion is configured to be extremely flexible as will be appreciated, but retain sufficient axial strength to help prevent distal tip separation on withdrawal of the guidewire from a position where the tip may be stuck in the anatomy, and to assist in facilitating pushability of the distal tip portion 511 of the guidewire.

With reference to FIG. 15, the underlying structure mentioned before will now be described. A medial coil 532 is attached to the core wire 501 at the third transition portion 524. The medial coil has an outer diameter substantially equal to the inner diameter of the proximal coil 508 and the inner diameter of the micromachined tubing 514. It is attached by soldering, and this location of attachment on the third transition portion is that of the medial solder and glue joint mentioned above. Also, it will be noted that the location is near the proximal end of the third transition portion, so that the diameter of the core wire at this location is substantially the same as the second reduced diameter portion 528. As the core wire transfers torque to the micromachined tubing at this location as mentioned above, the location on the grind profile is important as it represents the "end of the line" for torque transmission through the core wire, and the diameter of the corewire is directly proportional to the amount of torsional force that can be transmitted, the location and diameter are chosen in conjunction with selection of the parameters of the micromachined tubing so that the "carrying capacity" for torque is substantially equal. A mis-match represents an inefficiency in this regard and is to be avoided unless for some design objective a discontinuity in torquability is desired at this point.

The medial coil 532 is formed of stainless steel in one embodiment, and has a proximal unwound portion 534 at its proximal end, to aid in more secure bonding to the core wire 501 as a longer length of coil wire can be bonded due to slight deformation thereby allowed to follow the grind profile. The medial coil has a distal unwound portion 536 which will be further described next below.

Turning to FIG. 16, a distal coil 538 is disposed over the third reduced diameter portion at the distal tip portion. The proximal end of the distal coil is provided with an unwound portion 540 which cooperates with the distal unwound portion 536 of the medial coil to form a secure interlock by intertwining of the coils, then soldering. As will be appreciated the distal coil can be of slightly larger diameter wire, due to the reduced grind profile it overlays, but the outside diameter is held to be slightly less than that of the inside diameter of the micromachined tubing (not shown) as will be described. The distal coil is formed of a radiopaque material in the illustrated embodiment to provide enhanced fluoroscopic visibility. Materials such as platinum, gold, palladium, dysprosium, as known in the art, are used for this purpose, and accordingly the increased diameter wire used provides more radiopacity when formed of such a material useful for this purpose. The distal coil thus acts as a marker to aid in navigation of the guidewire within the anatomy of a patient. As will be appreciated, the drawing figures are not to scale, and the distal coil can be considerably longer than the medial coil 532. The distal end of the distal coil is soldered to the core wire 501 adjacent the distal end 510 at the location of the distal solder and glue joint 518.

With reference to FIGS. 14, 15, 16, and 17, it will be appreciated that the guidewire 500 apparatus is assembled by attaching the medial spring 532 to the core wire, then attaching the distal (marker) coil 538 to the medial coil, then the proximal coil is slipped over the assembly and soldered to the core wire 501 at the proximal solder joint 512 and to the medial coil 532 at the location of the medial solder and glue joint 516. The solder used throughout is a silver or gold alloy solder or another material regulatory-approved for such use.

With reference to FIG. 18, fabrication of the catheter is completed by placement of the micromachined tubing 514 over the distal tip portion 511. It is fixed in place by securing it at its proximal end at the medial solder and glue joint 516 by means of a suitable adhesive such as a UV cured regulatory-approved adhesive such as Dymax, and by attaching the distal end to the distal tip of the core wire 501, and also to the distal (marker) coil by an identical or similar adhesive. As mentioned this adhesive when cured forms a rounded tip 520 to reduce trauma, and completes the distal solder and glue joint which holds together the core wire, distal marker coil, and the micromachined tubing at the distal end 510 of the guidewire.

The guidewire can further include a micromachined "barcode" identification 142 located at a convenient location such as adjacent the proximal or distal end of the guidewire. The barcode is made by very lightly scoring the surface to form a binary code to encode identifying information regarding the catheter. This is done by a similar process to that used to micromachine the tubing 514 or another guidewire as discussed above and as follows. The advantage of such a marking system is that individual guidewires can be identified, enabling "lot of one" custom manufacturing and marking of one to as many as desired guidewires 500.

Figure 19:
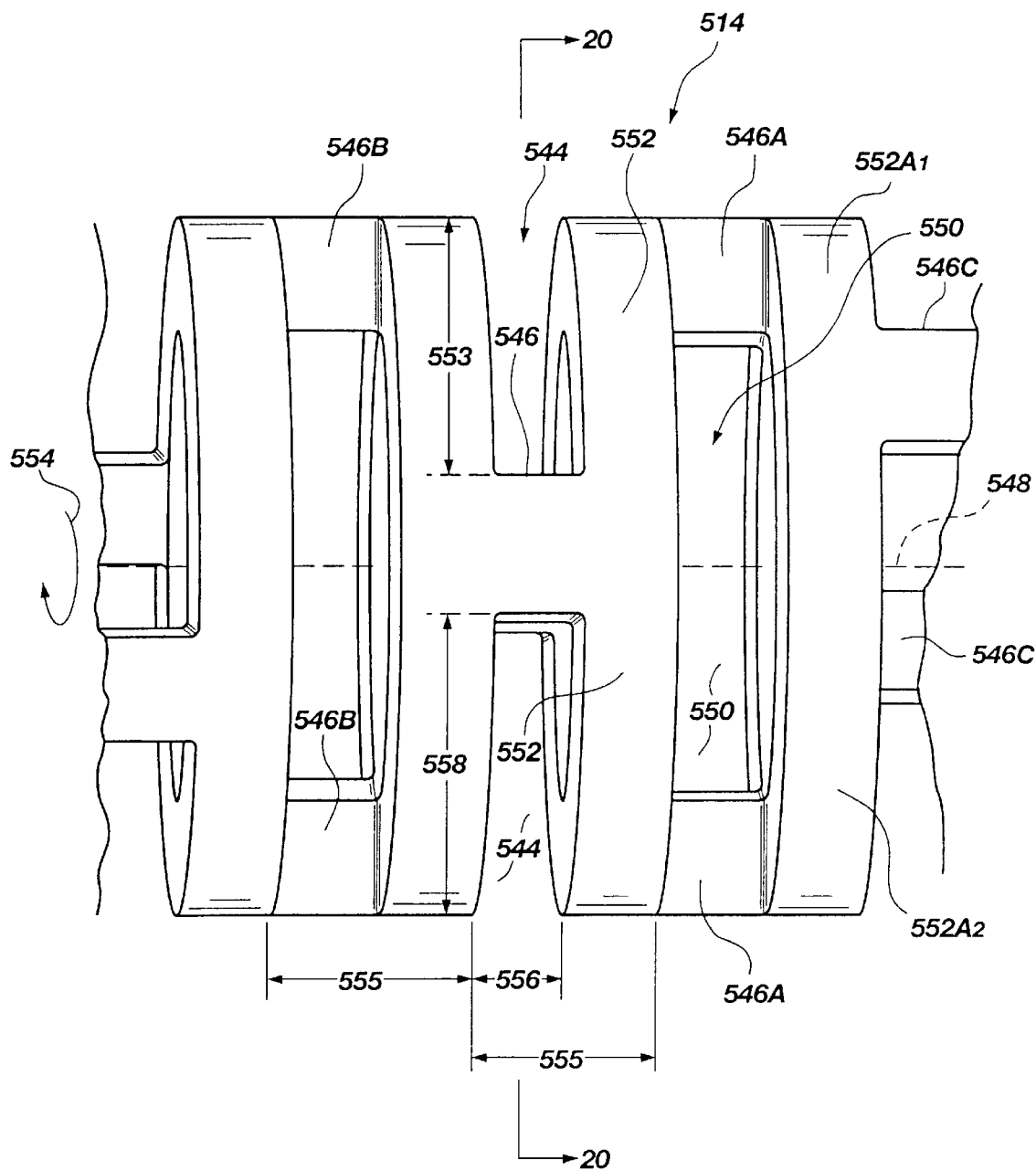
FIG. 19 shows a fragmentary perpsective view of a portion of a micromachined tubing segment such as shown in FIG. 18, in accordance with principles of the invention.

Turning now to FIG. 19, discussion of the micromachined tubing 514 more specifically should include mention of how the tubing is made. In addition to the description above with regard to wires generally, and below with regard to this tubing segment specifically, further details regarding fabrication of the tubing can be found in copending U.S. patent application Ser. No. 09/470,606, the disclosure of which is hereby incorporated herein by reference.

As will be appreciated, enhanced performance is obtained by optimization of one or more physical attributes of the guidewire. In the case of the illustrated exemplary embodiment now being discussed, a unique construction combined with optimization provides increased torquability while allowing flexure, so as to be compliant with tortuous vasculature in accessing a target site within the patient's anatomy.

For the moment digressing to review of a more general case, as mentioned above when a member of circular cross section is used to transmit a torsional force, the overwhelming majority of the force is "transmitted" by the outer portions of the member, the capacity to resist deformation due to induced stress being maximum at the outer circumferential surface of the member. Accordingly, whether a tubular member or a solid member of circular cross-section of a given material is used to transmit torque, relatively little increase in diameter for the tubular member is required to transmit the same amount of torque because in fact the "middle" portion of a solid circular member contributes comparatively little to resistance of the stresses, and hence does little to transmit them.

The present invention is directed to maximizing torque transmission, while minimizing resistance to bending of a guidewire body, for example in the tubular member 514 shown. To do so, from the forgoing it will be apparent that only the equivalent of a tubular structure is implicated, even though a solid member may be used. Therefore the following discussion will apply to solid wires as well, though it will be understood that this is because an assumption is made that the inner portion of the wire is not contributing appreciably, and the structure other than a tubular portion of it is being ignored. In practice a tubular configuration is advantageous as other structure can be placed inside, as in the case of the illustrated embodiment given by example herein employing a tubular micromachined tubing segment 514 at a distal tip portion 511.

Figure 20:
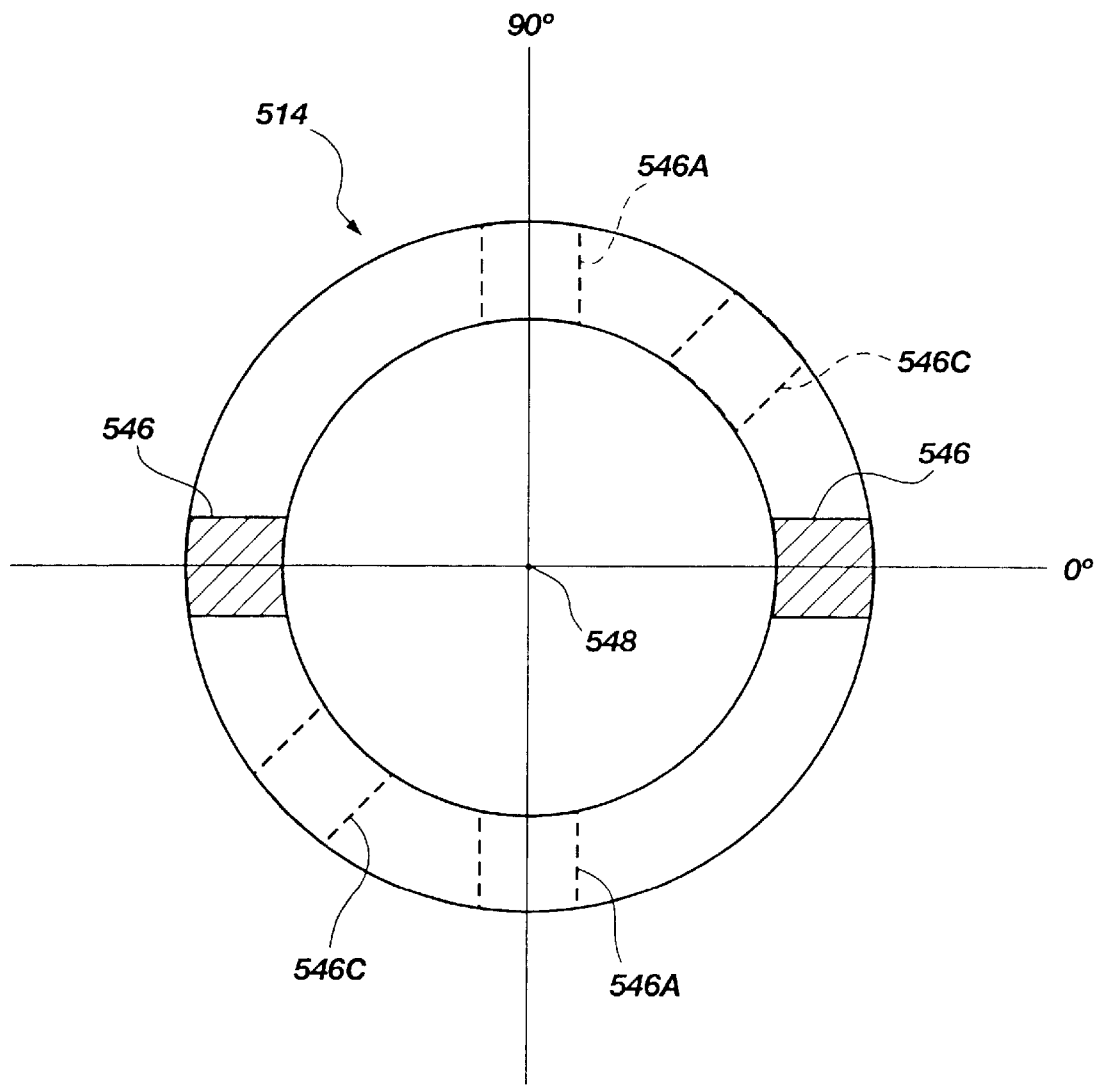
FIG. 20 shows a crossectional view, taken along line 20—20 in FIG. 19 of the micromachined tube shown in FIG. 19.

One way in which the guidewire distal portion is optimized is using superelastic material, preferably formed as a tube, micromachining the tube to create a structure which maximizes torque transmission while minimizing resistance to bending. A section of micromachined tubing 514, having slot-like cuts formed therein is shown to illustrate the structure. The cuts are opposed cuts in the illustrated embodiment. That is, two cuts are made from opposite sides of the tubing at the same location along the longitudinal axis of the tubing. The depth of the cuts is controlled to leave a segment 546 of the tubing wall extant between the cuts on each of the opposite sides (180 degrees apart) of the tubing. These segments will acts as "beams" as discussed above to carry forces across the cut area at that location along the longitudinal axis 548 of the tubing. As a matter of convention such segments will be referred to as "axial beams" 546 as they are disposed to carry or transfer forces in roughly an axial direction from adjacent structure on one side to adjacent structure on an opposite side. When a pair of opposed cuts 550 is made adjacent to the cuts previously described (544) the location of the cuts is made such that the axial beam(s) 546A formed by the second set of cuts is displaced circumferentially from the adjacent axial beam(s) 546. This of course is done by rotation of the tube through some angle relative to the saw used to cut the tubing before cutting. This can be seen in FIG. 20. The amount of rotation is selected with each successive cut to give a pattern calculated to facilitate torque transmission while also facilitating bending of the tube after machining and to mitigate whipping. The specifics of this cutting distribution will be discussed below. With reference again to FIG. 19, what is important to this discussion is that in addition to axial beams, other beams, which by convention we call transverse beams 552 are created.

The transverse beams 552 are defined in this example as the curved portion of the tubing wall between adjacent cuts 544, 550 and adjacent axial beams. e.g. 546 and 546A. As will be appreciated, these transverse beams carry forces from a particular set of axial beams to the two adjacent axial beams created by an adjacent set of cuts.

Figure 21:
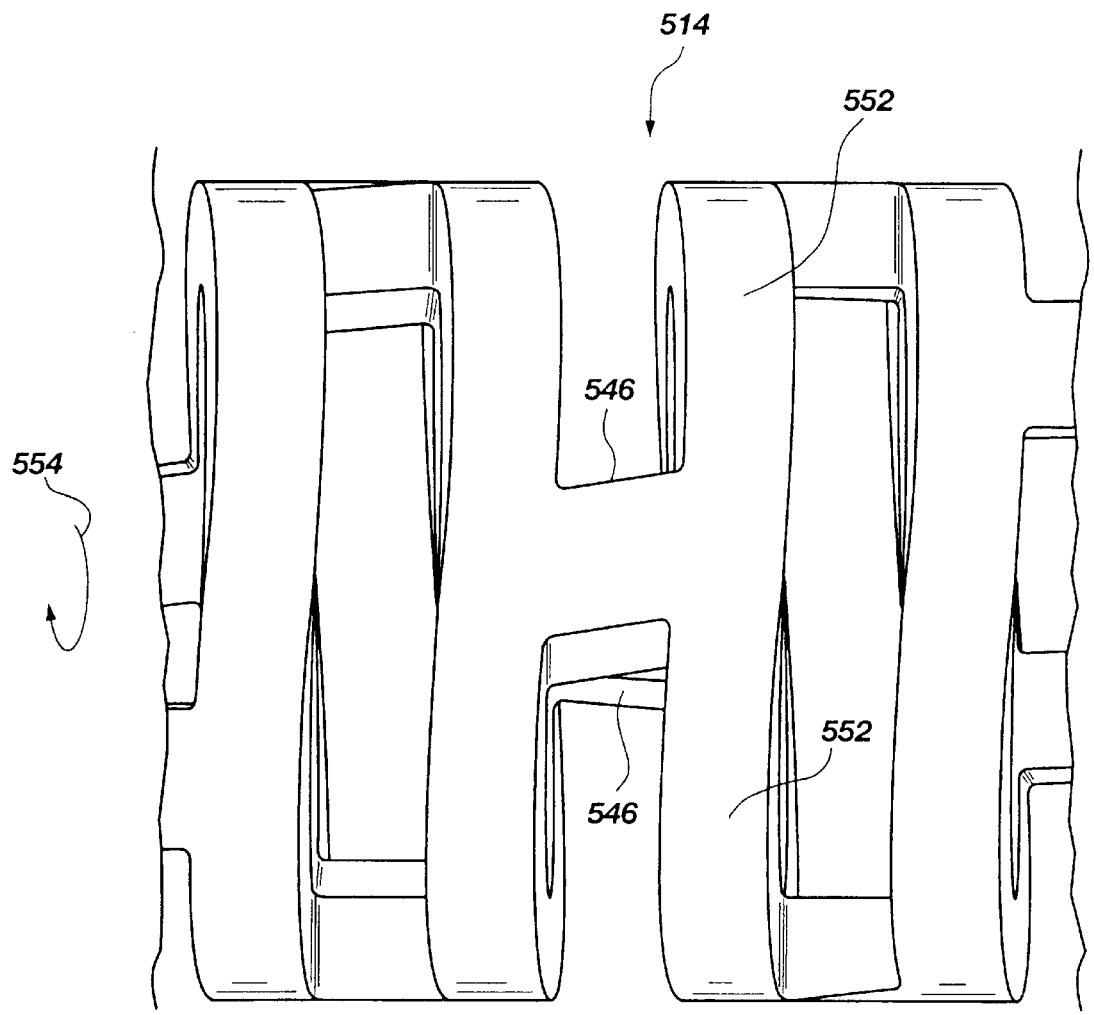
FIG. 21 shows a fragmentary perpsective view of a portion of a micromachined tubing segment such as shown in FIG. 19 subjected to torsional forces, illustrating deformation of the tubing.

With reference to FIG. 21, as will be appreciated once a tube 514 has been fabricated and a torquing force is applied at one end, say the proximal end, with respect to another, say the distal end, the forces in the machined tube will tend to deform the axial and transverse beams, e.g. 546 and 552. In order to optimize the machined tube for maximum torque transmission, the goal is to match, insofar as possible, the strain in the axial and transverse beams all along the length of the wire. This is so that one or the other will not constitute a weak point which will fail by deformation well beyond that of the adjacent axial or transverse beams when the torquing force is applied. As can be appreciated, with reference to FIG. 19 this matching can be done in tubing of constant cross section by variation of several parameters, namely the location (spacing 555 between), width 556, and depth 558 of cuts (e.g. 544, 550) made. Wider spacing of cuts creates wider transverse beams, shallower cuts create wider axial beams. Likewise more closely spaced cuts create narrower transverse beams, and deeper cuts create more narrow axial beams. Wider cuts create longer axial beams. The configuration of the micromachined tubing is defined by calculation, using well-known formulas for stress and stress/strain. The design process can further include finite-element analysis of the configuration to give localized stress and strain values. The calculations are repeated as necessary using incrementally changing parameters to optimize the design taking into account the concepts set forth herein.

Furthermore, another way of optimizing the design is to match, insofar as possible, the resistance to fatigue failure of the axial and transverse beams. This can be modeled, and can also be determined empirically. For example tubing samples can be spun in a tube having a bend therein, counting the revolutions to failure. Examination after failure will show failure by crack propagation through an axial or through a transverse beam. The relative geometries can be adjusted to balance the resistance to fatigue failure. Optimally the micromachined tubing will fail at a corner between an axial and transverse beam, as stress concentration there will control if the resistance to fatigue failure is sufficiently matched between the beam elements.

As a practical matter in manufacturing, a saw blade of a specified width will be used to make the cuts. And accordingly the width of all cuts is held to this value. In the illustrated embodiment a diamond silicon wafer cutting saw blade (as is used in the microprocessor and memory chip manufacturing art—not shown) about one thousandth of an inch wide is used to make the cuts (e.g. 544). While it is possible to make wider cuts by making a first cut, then moving the wire relative to the blade by a distance up to a width of the blade, and repeating as necessary for wider cuts, speed of fabrication is higher if a single cut is used. Therefore, using this constant cut width, the possible variables are depth 558 of cut and spacing 555.

Given that cut width 556 is to be held constant, in one embodiment the other parameters are selected as follows. The bending stiffness desired at any selected location along a length of tubing is obtained by selection of an appropriate spacing 555 between cuts. Given that the width of cut is a constant, in the calculations, selection of a distance between the set of opposed cuts to be made (e.g. 546A) and the last set of opposed cuts made (e.g. 546) will define, by means of the calculations, the depth of the cuts to be made as the distance between cuts defines the width of the transverse beams, and the width of the transverse beams is related to the width of the axial beam by the condition of equality of strain values to be obtained for a given applied torsional force 554 as mentioned.

The locations of the axial beams 546 will be set by the relative angular displacement of the adjacent sets of opposed cuts, as will be described, and hence the width and the length of the transverse beams 552 will be known. The width of the axial beams to be created depends on the depth of cut. The length of each axial beam is the same and equal to the constant cut width (e.g. one thousandth of an inch in the illustrated embodiment). The depth of cut is determined by comparison of the strain in the each of the resulting axial beams (they are assumed to be the same, though in fact they may not be in all cases due to differing force distribution due to variations in geometry) and then matching the strain in the axial beam(s) (e.g. 546) with the strain in the transverse beam(s) (e.g. 552). As will be appreciated, four transverse beams are created between each set of opposed cuts. The resulting strains are evaluated in each of the four beams, but in one embodiment another simplifying assumption is made that the strain in the two shorter transverse beams is the same, and likewise the strain in the two longer transverse beams is the same. The greater of the resulting strains in the transverse beams is compared with the strain in the axial beams. This represents the force transmission path for transfer of the torque. The depth of cut 558 is varied until the strains are matched. This value is then used in making the cuts at that location.

Other factors are taken into consideration. For example, there is a practical limit on the size of axial and transverse beams. Too large at the desired advantages are lost, too small and imperfections in materials and variations within the tolerances in machining can compromise performance. This may be governed by the thickness of the tubing if tubing is used, the size of the saw blade, accuracy of the machining apparatus, etc. Generally speaking, axial or transverse beams having dimensions on a par with or smaller than the width of the cutting blade used to micromachine them are avoided.

Further refinement of the design can be by matching fatigue failure resistance as discussed above. Further reduction of opportunities for development of cracks in the material is desirable, and rounding of the corners of the structure to reduce stress concentrations, and polishing of the structure, by electropolishing or abrasives as described elsewhere herein, or some other method is desirable as it further rounds corners and polishes surfaces to reduce the probability of crack propagation.

The design process then, in summary, is in one embodiment to space the cuts (e.g. 544, 550) apart along the axis 548 of the tubing so as to provide bending as desired. The cuts will be closer together to give less resistance to bending, and more spaced apart to give more resistance to bending. (See, for example FIGS. 13 and 18, where the tubing segment 514 becomes more flexible toward the distal end 510 of the guidewire 500.) The stiffness can be controlled by means of variation of the spacing 555 of the cuts, the other parameters being selected as appropriate as described above. The bending stiffness of the tubing can vary along the longitudinal axis, for example being made to gradually become less stiff toward the distal end, by gradually decreasing the spacing between cuts as in the above example.

As discussed, the depth 558 of the cuts is calculated using stress/strain relationships to match the strain in the axial 546 and transverse 552 beams created. In one embodiment as the calculation progresses, the strain in the axial beams is matched to that of the greatest calculated in the previously calculated transverse beams. Alternatively another method could be employed, for example comparing the strain in a given axial beam 546A to that of the transverse beams 552, 552A on either side of the axial beam along the axis 548 of the tubing 514 to match the strain. In another embodiment the average of the highest strain values in transverse beams 552, 552A1, 552A2 (552A1 and 552A2 being of unequal length the strains may be markedly different), on either side can be used to match the strain in the axial beam 546A under consideration. As will be appreciated, varying the thickness of the axial beam(s) affects the forces transmitted to the transverse beams and therefore varies the stress and strain in the transverse beam; so, as a result, many iterations of these calculation steps can be required to optimize the design. Likewise, adjustment of the size of one set of axial and transverse beams will affect the stresses and strains in adjacent sets of axial and transverse beams, so additional calculations and re-calculations can be required to optimize by matching strain throughout all the adjacent axial and transverse beams. Practical considerations will require the use of a computer and appropriate algorithm programed therein to optimize these design parameters. Again, refinement of the design by taking into consideration resistance to fatigue failure, or making this the primary design consideration are additional approaches that can be taken.

With reference again to FIG. 20, the distribution of the orientation of adjacent cut pairs giving rise to the axial beams 546 left after the cuts are made, will now be discussed. The object is to provide a distribution of cut orientations along the length of the tubing that minimizes "preferred" bending directions of the micromachined tubing 514 giving rise to undesirable effects collectively referred to as "whip" or a deviation of expected rotational result at the distal tip of the guidewire from that expected by the user from rotational inputs made at the proximal end of the guidewire by turning the collet fixture 212.

Figure 22:
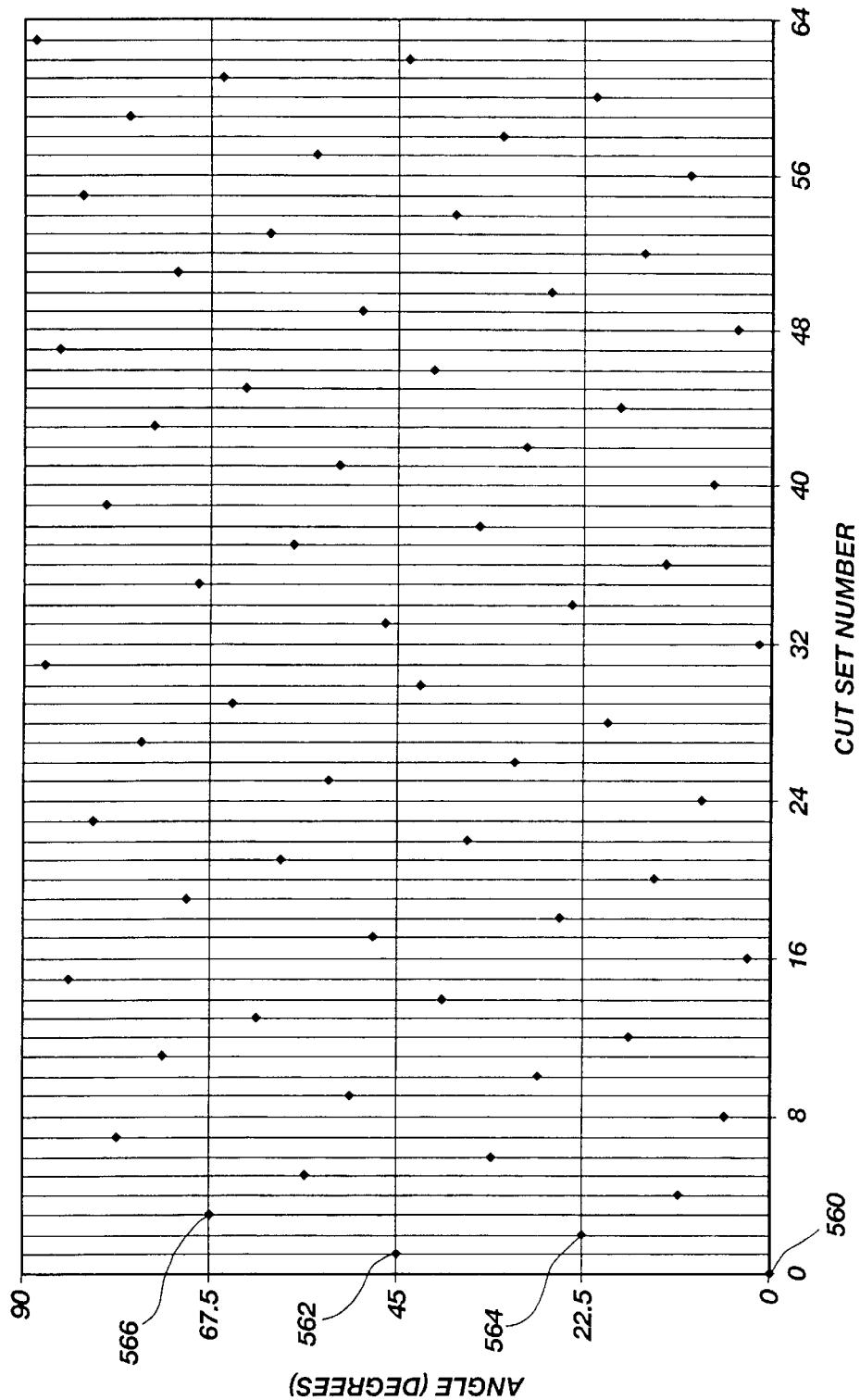
FIG. 22 shows a cut orientation distribution progressing in an axial direction along a micromachined guidewire segment.

With reference to FIG.22, one way of organizing the cut distribution to minimize whip is to assume a first cut pair of opposed cuts (180 degrees apart) and a second pair of opposed cuts immediately adjacent will be offset by an angle of ninety degrees. Collectively the four cuts will be referred to as a first cut set 560. A second cut set 562 of adjacent opposed cuts oriented ninety degrees apart is subsequently made, these being oriented with respect to the first cut set (designated arbitrarily as oriented at 0 degrees) so as to be rotated 45 degrees. The next similar cut set 564 is oriented at 22.5 degrees, and the next at 67.5 degrees, and so on in accordance with the distribution graphically illustrated in the figure. The sequence repeats every 64 cut sets (128 opposed cuts, and 256 cuts in total).

Figure 23:
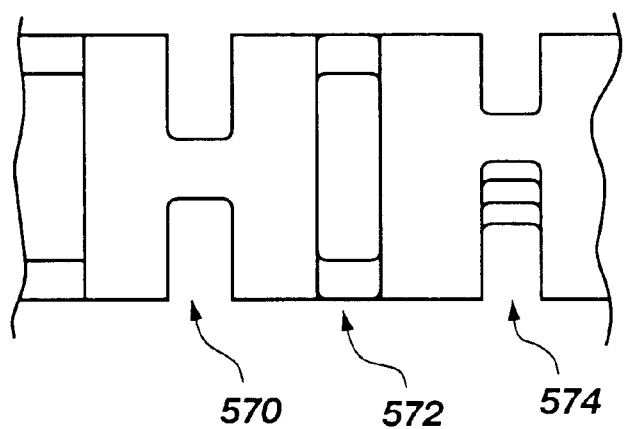
FIG. 23 shows a fragmentary side view of a portion of a micromachined tubing segment illustrating a cut orientation distribution in another embodiment.
Figure 24:
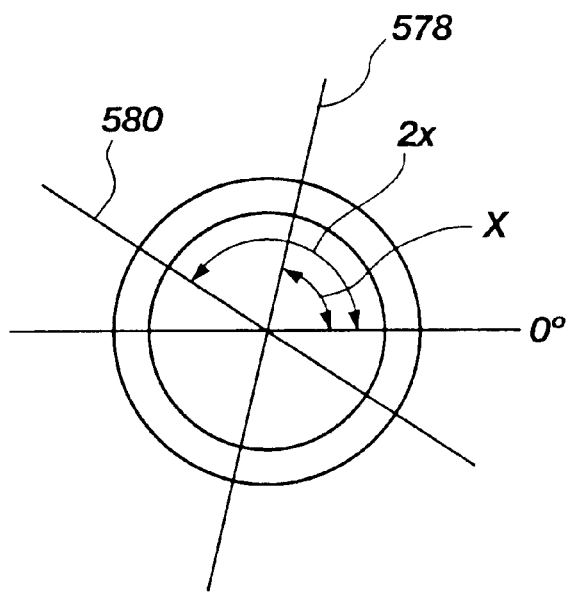
FIG. 24 shows a diagram further illustrating the cut set distribution shown in FIG. 23.

With reference to FIGS. 23 and 24, in another embodiment, the cut distribution is defined by a helical pattern. A first cut pair 570 is at zero degrees. A second cut pair 572 is rotated with respect to the first through a chosen angle "x". For example, this angle can be about 85 degrees. A third cut pair 574 is oriented by rotation through an angle equal to 2x, or 170 degrees in the exemplary embodiment. This pattern is continued, as the next cut pair (not shown) is oriented at 3x or 255 degrees, etc. continuing to turn in the same direction and by the same magnitude of angular rotation, x. The bending axis 576 formed by the first cut pair 570 is oriented at 0 degrees; and the next bending axis 578 formed by the second cut pair is oriented at 85 degrees in the example, and the third bending axis 580 at 170 degrees, and so on. The pattern will repeat after 72 cut pairs (144 total cuts) in the illustrated example where x is equal to 85 degrees. The orientation of any pair of cuts (and hence the bending axis) will be given by the following sequence: Pair 1=0 degrees; Pair 2=x degrees; Pair 3=2x degrees; Pair N=(N−1)x degrees. Where the increment is 85 degrees this is equivalent to 0; 85; 170; 255; . . . (N−1)85 . . . degrees. This has been found to give good bending and torque transmission characteristics and low whip. It also has the advantage of making the transverse beams approximately equal in length and this is advantageous in optimizing the design as will be appreciated.

With reference now to FIGS. 9, 10, 11 and 13 in comparing 0.014 inch diameter Ni Ti tubing micromachined as disclosed herein to conventional guidewire configurations and stainless steel tubing, it can be seen that the micromachined tubing is superior to conventional guidewire configurations when the diameter of the stainless steel core wire, which conventionally transmits the great majority of the torque, drops below about 5 thousandths of an inch on the grind profile. Since no advantage is obtained when the core wire is this diameter and larger, there is no reason to provide micromachined tubing proximal of the point where the grind profile drops to this value. Accordingly, for example in the illustrated embodiment it will be observed that where the medial solder/glue joint (516 in the FIGs.) is located is substantially at the point where the grind profile drops to about 0.005 inch diameter. As explained, the NiTi tubing segment which has been micromachined as described above provides a superior path for transmission of torque to the distal tip 510 of the guidewire from that point while at the same time facilitating bending. Thus the exemplary embodiment illustrates that the guidewire configuration can be optimized for cost as well, the less expensive stainless steel core wire and conventional coil configuration being provided up to the point where better characteristics are obtainable with a micromachined configuration.

Other features of the guidewire can include providing lubricious coatings on components distal of the proximal portion 502 previously described as including such a coating. For example a silicone coating as is known in the art can be applied in one of the many manners known in the art.

Another feature is that the micromachined tubing can be deburred after micromachining if necessary. For example an acid wash etching process can be used to deburr the inner surfaces, and the tubing can be placed on a mandrel and turned while being subjected to an abrasive jet to dauber and round the micromachined edges to minimize the possibility of catching on anatomy.

In another aspect, the micromachining pattern can be altered to provide preferred bending directions. This can be useful in customizing the guidewire to reach a target location within a particular anatomical structure, or even a particular individual patient. As an example of this, a MRI or CAT scan can produce a data set from which a preferred access route, for example vasculature to a target site, can be constructed in three dimensions. The guidewire can be micromachined to provide locally variable flexibility as needed to facilitate the traversing the last critical distance to the target site. A catheter individually customized for that patent could be made from that data set (for example sent to the manufacturer via the Internet) and shipped out to the user very rapidly, since micromachining is a computer-controlled automated process that could be customized based on the data set in accordance with another automated procedure. This guidewire (or catheter for that matter) could be individually identified by a bar code as described herein.

As will be appreciated the guidewire 500 system in accordance with principles of the invention enables improved performance over conventional configurations, and can be optimized for cost and performance. It is to be understood that the above-described exemplary embodiments and arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A guidewire system, wherein a guidewire is configured for introduction into a body lumen, comprising:
    a core wire having a proximal end, a distal end, and a tapering profile;
    a micromachined tube having a proximal end and a distal end, the micromachined tube being coupled to the core wire;
    a joint coupling the micromachined tube to the core wire;
    the location of the joint being at a location on the tapering profile where the torsional force which can be transmitted by the core wire and the torsional force which can be transmitted by the micromachined tube are substantially the same.

2. A guidewire system as in claim 1 wherein the micromachined tube further comprises a plurality of axial beams and a plurality of transverse beams.

3. A guidewire system as in claim 2, wherein the axial beams and the transverse beams are configured so that a maximum torsional strain is substantially the same both in the axial beams and the transverse beams.

4. A guidewire system as in claim 2, wherein the axial beams and the transverse beams are configured so that a resistance to fatigue failure is substantially the same in both the axial beams and the transverse beams.

5. A guidewire system as in claim 4, wherein the micromachined tube further comprises a polished surface.

6. A guidewire system as in claim 4, wherein corners of the beams are rounded so as to reduce stress concentrations.

7. A guidewire system as in claim 5, wherein the micromachined tube is electropolished.

8. A guidewire system as in claim 1, wherein the proximal end of the micromachined tube is located adjacent the joint.

9. A guidewire system as in claim 8, wherein the core wire extends distally of the joint and the distal end of the core wire is coupled to the micromachined tube.

10. A guidewire system as in claim 9, wherein the core wire and the micromachined tube are joined at their respective distal ends.

11. A guidewire system as in claim 10, further comprising a plurality of axial beams and a plurality of transverse beams configured so that a maximum torsional strain is substantially the same in both the axial beams and the transverse beams.

12. A guidewire system as in claim 11, wherein resistance to fatigue failure is substantially the same in the axial and transverse beams.

13. A guidewire system as in claim 1, further comprising a coil disposed between the core wire and the micromachined tube.

14. A guidewire system as in claim 1, wherein the micromachined tube is configured so its lateral flexibility varies with position along its length.

15. A guidewire system as in claim 14, wherein the flexibility of the micromachined tube increases toward its distal end.

16. A guidewire system as in claim 14, where the flexibility of the micromachined tube sequentially increases, then decreases, then increases with a change in position along its length.

17. A guidewire system as in claim 1, wherein the joint is located intermediate the proximal and distal ends of the micromachined tube.

18. A guidewire system as in claim 1, wherein the guidewire further comprises a proximal coil having a proximal end and a distal end, the proximal coil being disposed over the core wire and coupled thereto at the proximal end of the proximal coil, at least a portion of the proximal coil being disposed proximally of the micromachined tube.

19. A guidewire system as in claim 18, wherein at least a portion of the proximal wire adjacent its distal end is disposed between the micromachined tube and the core wire.

20. A guidewire system as in claim 19, further comprising a medial coil, said medial coil having a proximal end and a distal end, said medial coil being disposed between the micromachined tube and the core wire.

21. A guidewire system as in claim 20, wherein the medial coil has an unwound portion adjacent its proximal end and the proximal coil has an unwound portion adjacent its distal end, said unwound portions of the respective medial and proximal coils overlapping and being wound together to provide a mechanical interlock between the proximal coil and the medial coil, the micromachined tube overlaying the overlapping portions.

22. A guidewire system as in claim 21, where the overlapping portions are located adjacent the joint.

23. A guidewire system as in claim 22, further comprising a distal coil, the distal coil being coupled to the medial coil and to the core wire, the distal coil being disposed between the core wire and the micromachined tube.

24. A guidewire system as in claim 1, wherein the core wire has a first outer diameter along a substantial portion of its length, and the micromachined tube has an outer diameter substantially the same as the first outer diameter of the core wire over at least a portion of its length.

25. A guidewire system as in claim 1, further comprising a proximal coil disposed over the core wire proximal of the micromachined tube, the core wire having a first outer diameter along a substantial portion of its length, the proximal coil having substantially the same outer diameter as the first outer diameter of the core wire, and the micromachined tube having substantially the same outer diameter as the proximal coil.

26. A guidewire system, wherein a guidewire is configured for introduction into a body lumen, comprising:
  a core wire having a proximal end and a distal end and a tapering profile including a transition where a diameter of the core wire changes from a first outer diameter proximally to a second smaller outer diameter distally;
  a micromachined tube having a proximal end and a distal end, the micromachined tube being coupled to the core wire adjacent the transition;
  a joint coupling the micromachined tube to the core wire;
  a location of the joint being adjacent the transition, and wherein the torsional force which can be transmitted by the core wire and the torsional force which can be transmitted by the micromachined tube are substantially the same adjacent the joint.

27. A guidewire system as in claim 26, wherein the core wire has a first outer diameter proximal of the joint and wherein the micromachined tube has an outer diameter substantially the same as the first outer diameter.

28. A guidewire system as in claim 26, wherein the guidewire further comprises a proximal coil having a proximal end and a distal end, and the core wire having a proximal transition located proximal to the transition adjacent the joint, the proximal end of the proximal coil being coupled to the core wire adjacent the proximal transition and the distal end being adjacent the joint, whereby the outer diameter of the guidewire is substantially the same along the guidewire.

29. A guidewire system as in claim 27, wherein the proximal coil further comprises a portion adjacent its distal end having a smaller outer diameter than the first outer diameter, the micromachined tube overlying at least a portion of the proximal coil adjacent the distal end of the proximal coil.

30. A guidewire system as in claim 26, wherein the micromachined tube further comprises a plurality of axial beams and a plurality of transverse beams.

31. A guidewire system as in claim 29, wherein the axial beams and the transverse beams are configured so that a maximum torsional strain is substantially the same in both the axial and the transverse beams.

32. A guidewire system as in claim 29, wherein the axial beams and the transverse beams are configured so that a resistance to fatigue failure is substantially the same in the axial and the transverse beams.

33. A guidewire system as in claim 31, wherein the micromachined tube further comprises a polished surface.

34. A guidewire system as in claim 29, wherein the corners of the beams are rounded so as to reduce stress concentrations.

35. A guidewire system as in claim 26, wherein the core wire extends distally of the joint and the distal end of the core wire is coupled to the micromachined tube.

36. A guidewire system as in claim 34, wherein the core wire and the micromachined tube are joined at their respective distal ends.

37. A guidewire system as in claim 26, further comprising plurality of axial beams and a plurality of transverse beams configured so that a maximum torsional strain is substantially the same in the axial and the transverse beams.

38. A guidewire system as in claim 37, wherein resistance to fatigue failure is substantially the same in the axial and transverse beams.

39. A guidewire system as in claim 26, wherein the micromachined tube is configured so its lateral flexibility varies with position along its length.

40. A guidewire system as in claim 26, wherein the guidewire further comprises a proximal coil having a proximal end and a distal end, the coil being disposed over the core wire and coupled thereto at the proximal end of the proximal coil, at least a portion of the proximal coil being disposed proximally of the micromachined tube.

41. A guidewire system as in claim 28, further comprising a medial coil, said medial coil having a proximal end and a distal end, said medial coil being disposed between the micromachined tube and the core wire.

42. A guidewire system as in claim 41, wherein the medial coil has a proximal unwound portion adjacent its proximal end and the proximal coil has an unwound portion adjacent its distal end, said unwound portions overlapping and being wound together to provide a mechanical interlock between the proximal coil and the medial coil, the micromachined tube overlaying the overlapping portions.

43. A guidewire system as in claim 42, where the overlapping portions are located adjacent the joint.

44. A guidewire system as in claim 43, further comprising a distal coil, the distal coil being coupled to the medial coil and to the core wire, the distal coil being disposed between the core wire and the micromachined tube.

45. A guidewire system, the guidewire being configured for guideably traversing a body lumen, comprising:
  a core wire having a proximal end, a distal end, and an outer diameter, and a transition intermediate the proximal and distal ends where the outer diameter changes from a larger diameter proximally to a smaller diameter distally;

a micromachined tube having a proximal end and a distal end, said micromachined tube further comprising a plurality of axial beams and a plurality of transverse beams, the beams being configured so that resistance to fatigue failure of the axial beams and of adjacent transverse beams is substantially the same, the micromachined tube being disposed over the core wire and coupled to the core wire adjacent the transition;

the core wire having a capacity to transmit torsional force that is substantially the same as a capacity to transmit torsional force of the micromachined tube adjacent the transition;

whereby the capacity of the guidewire to transmit torsional forces is substantially maintained from that of the core wire proximal of the transition to that distal of the transition where the core wire has a smaller outer diameter and at least a portion of the torsion forces are carried by the micromachined tube.

46. A guidewire system as in claim 45, wherein the core wire extends distally of the transition to the distal end of the micromachined tube and wherein the micromachined tube is coupled to the core wire adjacent the distal end of each.

47. A guidewire system as in claim 46, further comprising a proximal coil having a proximal end and a distal end, the proximal coil being disposed over the core wire proximally of the micromachined tube.

48. A guidewire system as in claim 47, further comprising a proximal transition, and wherein the proximal end of the proximal coil is coupled to the core wire adjacent the proximal transition, and the distal end of the proximal coil is coupled to the core wire adjacent the transition where the micromachined tube is coupled to the core wire.

49. A guidewire system as in claim 48, wherein an outer diameter of the guidewire is not substantially increased along the length thereof from the proximal end to the distal end.

50. A guidewire system as in claim 45, wherein the axial beams and the transverse beams are configured so that a maximum strain occurring in either of the axial or transverse beams from torsion and bending forces is substantially the same.

51. A method of enhancing performance of a coronary guidewire is given by undertaking steps comprising:

providing a micromachined tube, said tube having a plurality of axial beams and a plurality of transverse beams;

configuring the micromachined tube so that a maximum strain induced in the axial beams from torsion and bending of the micromachined tube is substantially the same as that in the transverse beams;

providing a core wire having a diameter profile and a transition from a first diameter proximally to a second smaller diameter distally, coupling the micromachined tube to the core wire adjacent the transition;

selecting diameters of the profile and the position of the coupling of the micromachined tube to the core wire so that a torque transmission capacity of the core wire is substantially the same as a torque transmission capacity of the micromachined tube adjacent the location of the coupling.

52. A guidewire system wherein improvement of performance of a coronary guidewire is given by undertaking steps comprising:

providing a micromachined tube, said tube having a plurality of axial beams and a plurality of transverse beams;

configuring the micromachined tube so that resistance to fatigue failure of an axial beam from torsion and bending of the micromachined tube is substantially the same as an adjacent in transverse beams;

providing a core wire having a diameter profile and a transition from a first diameter proximally to a second smaller diameter distally, coupling the micromachined tube to the core wire adjacent the transition;

selecting diameters of the profile and the position of the coupling of the micromachined tube to the core wire so that a torque transmission capacity of the core wire is substantially the same as a torque transmission capacity of the micromachined tube adjacent the location of the coupling.

53. A guidewire system as in claim 52, further comprising the step of rounding corners of the axial and transverse beams.

54. A guidewire system as in claim 53, further comprising the step of polishing the micromachined tube.

* * * * *

UNITED STATES PATENT AND TRADEMARK OFFICE
CERTIFICATE OF CORRECTION

PATENT NO.    : 6,579,246 B2
DATED         : June 17, 2003
INVENTOR(S)   : Stephen C. Jacobsen et al.

It is certified that error appears in the above-identified patent and that said Letters Patent is hereby corrected as shown below:

Column 2,
Line 45, replace "an" with -- a --.

Column 5,
Line 52, replace "influences" with -- influence --.

Column 6,
Line 20, after "wire" add -- to --
Line 63, delete "is".

Column 10,
Line 49, replace "150" with -- 510 --.

Column 13,
Line 13, replace "forgoing" with -- foregoing --.

Column 15,
Line 25, replace "at" with -- and --.

Signed and Sealed this

Thirteenth Day of April, 2004

JON W. DUDAS
*Acting Director of the United States Patent and Trademark Office*